United States Patent [19]

Lee

[11] Patent Number: 4,935,539

[45] Date of Patent: Jun. 19, 1990

[54] METHOD FOR INCREASING YIELD AND PRODUCT QUALITY WHILE REDUCING POWER COSTS IN OXIDATION OF AN AROMATIC ALKYL HYDROCARBON TO AN AROMATIC CARBOXYLIC ACID

[75] Inventor: Myon K. Lee, Wheaton, Ill.

[73] Assignee: Amoco Corporation, Chicago, Ill.

[21] Appl. No.: 339,471

[22] Filed: Apr. 17, 1989

Related U.S. Application Data

[62] Division of Ser. No. 169,457, Mar. 17, 1988.

[51] Int. Cl.$^5$ ............................................. C07C 51/265
[52] U.S. Cl. ..................................... 562/412; 422/224; 562/414
[58] Field of Search ....................... 562/412; 422/224

[56] References Cited

U.S. PATENT DOCUMENTS

| | | | |
|---|---|---|---|
| 3,660,476 | 5/1972 | Ichikawa et al. | 562/412 |
| 4,327,226 | 4/1982 | Shigeyasu et al. | 562/416 |
| 4,339,599 | 7/1982 | Jongsma | 562/412 |
| 4,357,475 | 11/1982 | Hanotier et al. | 562/414 |

*Primary Examiner*—Werren B. Lone
*Assistant Examiner*—Vera C. Clarke
*Attorney, Agent, or Firm*—Gunar J. Blumberg; William K. Magidson; Ralph C. Medhurst

[57] ABSTRACT

A continuous stirred-tank reactor suitable for the liquid-phase oxidation of an aromatic alkyl to an aromatic carboxylic acid is provided with vertically disposed, relatively narrow baffles on the reactor wall and with oxidizing gas inlet means below the agitator in the reactor. The baffle width is about 0.02 to about 0.04 times the diameter of the reactor.

1 Claim, 2 Drawing Sheets

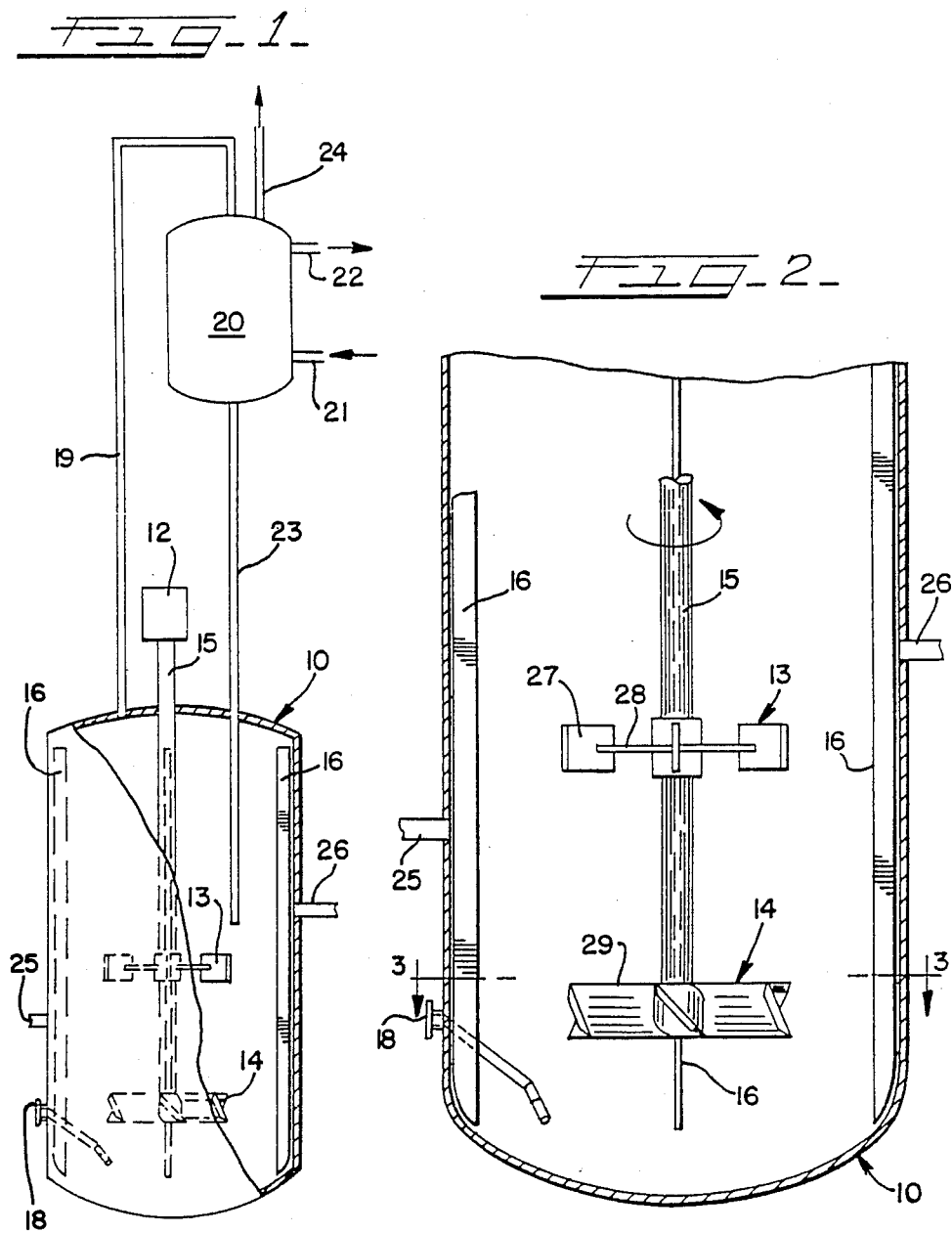

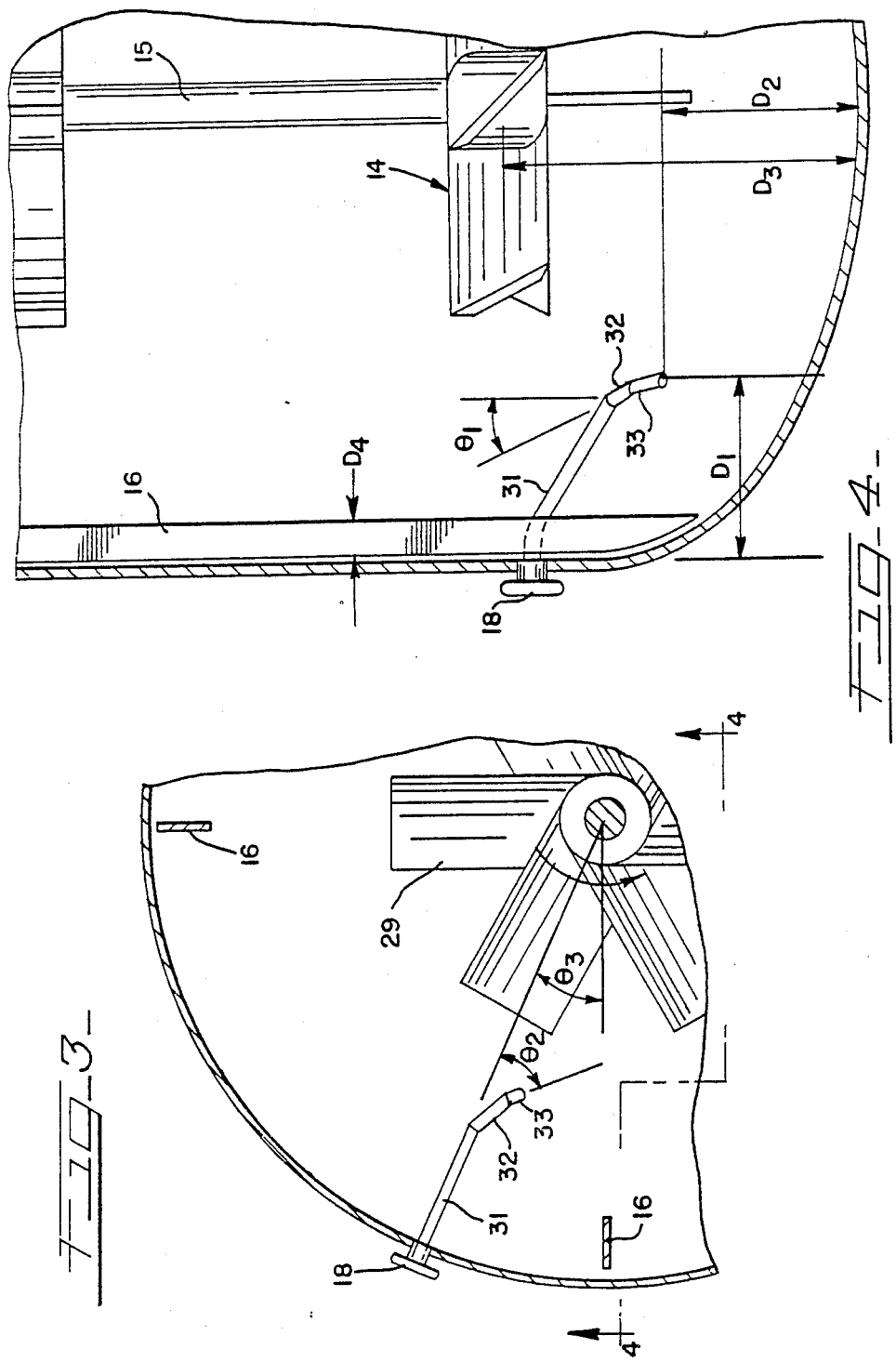

METHOD FOR INCREASING YIELD AND PRODUCT QUALITY WHILE REDUCING POWER COSTS IN OXIDATION OF AN AROMATIC ALKYL HYDROCARBON TO AN AROMATIC CARBOXYLIC ACID

This is a division, of application Ser. No. 169,457, filed Mar. 17, 1988.

FIELD OF THE INVENTION

This invention relates generally to a process for a liquid-phase oxidation of an aromatic alkyl hydrocarbon to an aromatic carboxylic acid, and principally to a liquid-phase oxidation of paraxylene to terephthalic acid. More particularly, the present invention concerns a method and apparatus for increasing reactor conversion efficiency, for reducing power costs, as well as for improving the aromatic carboxylic acid product quality.

BACKGROUND OF THE INVENTION

Liquid-phase oxidation of an aromatic alkyl hydrocarbon to an aromatic carboxylic acid is a highly exothermic chemical reaction. Volatilizable aqueous acidic solvents are used to contain the reaction mixture and to dissipate the heat of reaction. The oxidation of aromatic alkyl hydrocarbons in the liquid phase to form aromatic carboxylic acids is generally performed in a vented, well-mixed oxidation reactor, with a substantial portion of the heat generated by the exothermic oxidation reaction being removed by refluxing a portion of the aqueous solvent and aromatic alkyl hydrocarbon contained within the reactor.

The optical quality of the produced aromatic carboxylic acid is dependent to a large extent on the mixing that takes place in the oxidation reactor inasmuch as reactor mixing disperses the reactants, promotes oxygen mass transfer, and keeps the produced aromatic carboxylic acid in suspension. Uniform dispersion of the reactants and the efficiency of oxygen mass transfer influence the oxidation rate of the aromatic alkyl hydrocarbon and produced intermediate compounds, as well as the formation of undesirable optical impurities and by-products. This, in turn, influences the optical quality of produced aromatic carboxylic acid, reactor burning, and reaction yield. Accordingly, there are significant economic incentives for improving reactor mixing performance.

The materials vaporized as a result of the heat generated in the exothermic reaction, together with unreacted oxygen and other noncondensable components that may be present, pass upwardly through the reactor and are withdrawn from the reactor at a point above the reaction mixture liquid level in the reactor. The vapors are passed upwardly and out of the reactor to an overhead reflux condenser system where the vaporized solvent, water and aromatic alkyl are condensed. The condensed materials, now at a temperature less than the reactor contents' temperature, are returned to the reactor by gravity. The noncondensable gases, carried along with the vaporized reactor material, are vented.

In operation, the reactor is fed by a liquid feed stream containing the aromatic alkyl hydrocarbon, aqueous acidic solvent and an oxidation catalyst. An oxygen-containing gas is separately introduced into the reactor for oxidizing the aromatic alkyl hydrocarbon to the aromatic carboxylic acid in the presence of the catalyst.

The reaction mixture contained in the reactor includes a suspension of the produced aromatic carboxylic acid. Since the reaction mixture contains solid-phase and liquid-phase components, as well as the continuously introduced oxygen-containing gas, vigorous stirring of the reactor contents is necessary to maintain the desired uniform reactor conditions and to obtain a high quality product. The vigorous stirring is costly in terms of power input; however. Also, even with high power input the mixing effectiveness of prior systems has not been as good as desired.

In one system for the production of an aromatic carboxylic acid, the reaction takes place in a vertically disposed elongated vessel having a substantially cylindrical sidewall and having an agitator mounted for rotation within the vessel on a shaft at about the axis of the vessel. The agitator has dual impellers with an upper mixing element, or impeller, in the form of a 4-blade disc turbine at an intermediate location on the shaft and a lower mixing element, or impeller in the form of a 4-blade turbine with pitched blades at the lower end of the shaft.

The reactor in this system has four vertical baffles substantially evenly spaced on the cylindrical vessel walls. Each baffle is of rectangular cross-section and has a width of about 1/12 of the vessel inside diameter. Each baffle is spaced from the vessel wall by a clearance of about 1/100 of the vessel diameter. Gas introduction in such a system heretofore has been at a level somewhat higher than the level of the lower impeller.

The present invention provides an oxidation reactor having enhanced mixing performance. Gas hold-up in the reactor is increased and the power required to maintain solid reaction products in suspension is substantially reduced. As a result, an aromatic carboxylic acid product of relatively higher quality can be obtained.

SUMMARY OF THE INVENTION

The present invention contemplates an oxidation reactor which is a generally cylindrical, upstanding pressure vessel provided with an axially mounted agitator having an upper impeller element at about the midpoint of the reactor and a lower-most impeller element at about the bottom of reactor, with vertically disposed baffles adjacent to but spaced from the reactor wall, and with gas inlet means terminating in a plurality of nozzles within the reactor below the lowermost impeller element. The vertically disposed baffles are spaced from and extend radially inwardly from the reactor wall and have a width of about 0.02 to about 0.04 times the reactor inside diameter. The gas inlet nozzles preferably are positioned about midway between the lowermost impeller element and the reactor bottom.

BRIEF DESCRIPTION OF THE DRAWINGS

FIG. 1 is a schematic diagram, partly in cross-section, showing the general configuration of the reactor of this invention;

FIG. 2 is an enlarged schematic cross-sectional view of the reactor (with upper end thereof broken away), showing the general spatial relationship of the reactor elements;

FIG. 3 is an enlarged horizontal cross-sectional view of a single quadrant of the reactor, through Section 3—3' of FIG. 2, showing the placement of the gas nozzles and baffles relative to each other and relative to the swept diameter of the lowermost impeller; and FIG. 4 is an enlarged vertical cross-sectional view, through Section 4—4' of FIG. 3, of one side of the lower portion of the reactor showing the placement of the air nozzles relative to the bottom of the reactor and relative to the lowermost impeller.

DETAILED DESCRIPTION OF PREFERRED EMBODIMENTS

Aromatic carboxylic acid is produced in an oxidation reactor at an elevated temperature and pressure by liquid-phase oxidation of an aromatic alkyl hydrocarbon by an oxygen-containing gas in a vaporizable solvent medium. Oxidation of the aromatic alkyl hydrocarbon to the aromatic carboxylic acid takes place in an aqueous acidic solvent medium in the presence of an oxidation catalyst. The conversion of aromatic alkyl hydrocarbon to aromatic carboxylic acid is exothermic. Heat generated by the oxidation reaction is at least partially removed by vaporization of a portion of the solvent, water, aromatic alkyl hydrocarbon and other vaporizable constituents of the reaction mixture present in the oxidation reactor. Vaporized reaction mixture constituents are withdrawn from the oxidation reactor, condensed in an overhead condenser system, and fed back into the oxidation reactor while uncondensed gases are vented from the system.

A liquid feed stream for the oxidation reactor contains the aromatic alkyl hydrocarbon, the solvent medium, and an effective amount of an oxidation catalyst for effecting in the reactor a liquid-phase oxidation of the aromatic alkyl hydrocarbon, in the presence of oxygen, to the corresponding aromatic carboxylic acid.

Referring to FIG. 1, an elongated, vertically-disposed, continuous, stirred-tank reactor 10 for oxidizing an aromatic alkyl hydrocarbon to an aromatic carboxylic acid is shown. The oxidation reaction proceeds in the liquid phase. The reactor 10 is a pressure vessel and includes an agitator 12 which drives upper mixing element, or impeller 13 and lowermost mixing element, or impeller, 14, both fixed to an agitator shaft 15. The reactor 10 further includes relatively narrow vertically disposed internal baffles 16 situated adjacent to the cylindrical reactor wall and extending radially inwardly therefrom. Each mixing element is rotated by the shaft 15 in a generally horizontal plane at a preselected rotational speed so that the contents of the reactor 10 are well-mixed, as discussed in greater detail below. Plural gas nozzles such as nozzle 18 are provided to introduce oxidizing gas below the lowermost impeller 14.

The contents of the reactor 10 are subjected to a temperature and elevated pressure sufficient to maintain the contained volatilizable solvent and aromatic alkyl hydrocarbon substantially in the liquid state.

An aromatic alkyl hydrocarbon, such as paraxylene, and a volatilizable aqueous acidic solvent medium, such as a catalyst-containing aqueous acetic acid solution, are combined to form a mixture, which enters reactor 10 through conduit 25. An oxygen-containing gas is introduced into the interior of the reactor 10 via a gas inlet line 18 which terminates within the reactor near the bottom thereof and below impeller 14. The, oxygen-containing gas serves to oxidize the aromatic alkyl hydrocarbon to an aromatic carboxylic acid in the presence of the catalyst. Liquid reaction products and solvent medium are removed through line 26.

Heat of reaction in the reactor 10 vaporizes the volatilizable solvent, water and reaction mixture contained therein. A substantial portion of the heat generated by the exothermic reaction in the reactor 10 is removed from the reaction mixture by vaporization of the aqueous solvent and, to a lesser extent, the aromatic alkyl hydrocarbon. The vaporized material and any unreacted oxygen and other components of the oxygen-containing gas fed to the reactor 10 pass upwardly in the reactor 10 and are withdrawn from the reactor 10 via the exit pipe 19. These vaporized materials and gases are received into an overhead condenser system, such as the condenser 20, through which a cooling fluid is circulated, entering through inlet 21 and discharging through outlet 22. A condensed portion of the vapors passing into condenser 20 is returned to the reactor through conduit 23; and an uncondensed portion is vented from the system through conduit 24.

In the reactor 10, the aromatic alkyl hydrocarbon is oxidized by oxygen, usually introduced as air, in the presence of the catalyst, to form the desired aromatic carboxylic acid and intermediates thereto. A product stream is withdrawn as an effluent stream from the reactor 10 via the discharge pipe 26. The product stream is thereafter treated using conventional techniques to separate its components and to recover the aromatic carboxylic acid contained therein, usually by further crystallization, solid-liquid separation and drying.

The distinctive features of the present invention are illustrated in greater detail in FIGS. 2 to 4. In FIG. 1 and the remaining FIGURES, like reference numerals have been assigned to like parts or elements. Further, for the sake of brevity, only those parts or elements of FIGS. 2 to 4 which have not been discussed in detail heretofore will be discussed at length hereinbelow.

Referring to FIG. 2, upper impeller element 13 comprises a six-blade disc turbine, in which each blade 27 is in a plane which is radial to shaft 15. The blades are evenly spaced from each other and each blade is connected to the inner shaft through disc 28.

It may also be seen in FIG. 2 that lower impeller element 14 comprises a six-blade pitched blade turbine, in which each blade 29 is pitched at an angle of about 45°. The blades are spaced evenly from each other. The direction of the 45° pitch is determined by the direction of rotation of shaft 15 so that liquid will be moved upwardly and outwardly from the shaft by each blade in the normal rotation of the shaft. In other words, each blade is arranged with its leading edge lower than its trailing edge in the direction of turbine rotation.

As stated above, oxygen-containing gas, usually air, is introduced into the interior of the reactor through gas inlet line 18. In the preferred embodiment, there are four similar gas inlet lines, one in each quadrant of the reactor; however, only one is shown in FIGS. 1 and 2 for clarity.

Each gas inlet line passes through the reactor wall at an elevated level within the reactor and then extends downwardly from the reactor wall to a level (as shown in FIG. 4) below the lowermost impeller. FIGS. 3 and 4 show plan and elevation respectively of line 18 comprising a plurality of straight pipes designated as 31, 32 and 33 fabricated to smoothly direct the gas to the desired location.

The distance between the nozzle tip and the reactor wall, shown as D1, preferably is about 0.23 times the inside diameter of the reactor vessel. The distance between the nozzle tip and the reactor bottom, shown as D2, is about 0.12 to about 0.18 times the inside diameter; and the distance between the lower impeller (measured at the center of its blades) and the reactor bottom, shown as D3, is in the range of about 0.25 to about 0.36 times the vessel diameter. Thus, the nozzle tips are at a level about midway between the reactor bottom and the lower impeller.

The downward nozzle angle ($\theta_1$) between the nozzle and a vertical reference line parallel to the longitudinal axis of the reactor (shown in FIG. 4) is in a range of about 15° to about 30°, preferably in a range of about 20° to about 25°; and the nozzle displacement angle from a plane extending radially from the longitudinal axis of the reactor ($\theta_2$) is in a range of about 30° to about 90°, preferably in a range of about 45° to about 70°; for a preferred gas stream direction which is approximately tangential to the circular area swept by the lower impeller.

FIGS. 3 and 4 also show the location of baffles 16 relative to the reactor wall and to each other as well as their location relative to the gas inlet conduits. The radial angle between a gas inlet conduit and the nearest baffle ($\theta_3$) is in a range of about 20° to about 45°, preferably in a range of about 25° to about 35°. Each of the baffle blades can be rounded or chamfered at its edge distal to the reactor sidewall.

The width of the baffles (D4 in FIG. 4) is about 0.02 to about 0.04 times the inside diameter of the reactor vessel. The spacing between each baffle and the vessel wall is about 0.01 times the inside diameter of the reactor vessel.

The improved results obtainable in accordance with this invention were demonstrated in a system similar to that described above except that the lower impeller had four rather than six 45° pitched blades and the test fluids were tap water and air at ambient conditions, with 15 weight percent of crude terephthalic acid as the solids content and an air flow rate of 2.0 volumes of air per minute per unit volume of slurry. This air flow rate was equivalent to a superficial gas velocity of about 5.3 feet/minute.

In this system, the substitution of the narrower baffles of the present invention for the relatively wider baffles heretofore used resulted in requiring 14% less agitator speed and 61% less power consumption at the minimum levels for complete suspension of the solids. In addition, gas holdup at an identical power input is increased by about 14%.

Changing location of the nozzle positions from above to below the lower impeller resulted in an increase of gas holdup of about 29%, albeit at a slight increase in required agitator speed and power. At the same power level, the gas holdup improvement was observed to be about 16%.

There was also observed a much better dispersion of gas bubbles in the lower impeller region. This effect is especially important in suppressing the formation of optical impurities because it is believed that the bulk of paraxylene oxidation occurs in the region of the lower impeller.

In the same system, the substitution of the narrower baffles and a 45° pitched blade turbine impeller with six blades as well as the changed location of the gas nozzle positions from above to below the lower impeller resulted in a reduction of agitator speed by 16% and a reduction of power consumption by 62%, measured at the minimum required for complete suspension of solids. At the same power input, the gas holdup improvement was observed to be about 38%.

The invention has been described with respect to a preferred embodiment thereof. It will be understood, however, by those skilled in the art that modifications may be made within the scope of the invention as defined in the claims.

I claim:

1. In the method of oxidizing an aromatic alkyl hydrocarbon to produce an aromatic carboxylic acid in which the hydrocarbon is maintained in a body of liquid within a vertically disposed vessel having an axis and a substantially cylindrical sidewall and having vertically disposed baffles on the sidewall while an oxygen-containing gas is passed through the body of liquid, in which oxidation a finely divided solid product is produced and is suspended in the body of liquid by the agitation of rotating impellers mounted on a vertical shaft substantially at the axis, the agitation being provided by a continuously supplied impetus at a mid-level in the liquid body to flow a portion of the liquid horizontally toward the cylindrical sidewall and rotationally around the cylindrical sidewall and by a continuously supplied impetus at a lower level in the liquid body to flow a portion of the liquid upwardly and outwardly toward the cylindrical sidewall and rotationally around the cylindrical sidewall in a path interrupted by the vertically disposed baffles, the improvement which comprises introducing the gas into the body of liquid at a level below the lowest impeller.

* * * * *